United States Patent [19]

Messerschmidt et al.

[11] Patent Number: 4,859,064
[45] Date of Patent: Aug. 22, 1989

[54] DIFFUSE REFLECTANCE SPECTROSCOPY SYSTEM AND METHOD

[75] Inventors: Robert G. Messerschmidt, Westport; Donald W. Sting, New Canaan, both of Conn.

[73] Assignee: Spectra-Tech, Inc., Stamford, Conn.

[21] Appl. No.: 191,980

[22] Filed: May 9, 1988

[51] Int. Cl.[4] ............................................. G01N 21/47
[52] U.S. Cl. ..................................... 356/446; 250/341
[58] Field of Search .............. 356/445, 446, 447, 448, 356/346; 250/341, 353

[56] References Cited

U.S. PATENT DOCUMENTS

| | | | |
|---|---|---|---|
| 3,229,564 | 1/1966 | Meltzer | 356/446 |
| 4,360,275 | 11/1982 | Louderback | 356/446 |
| 4,464,050 | 8/1984 | Kato et al. | 356/446 |
| 4,661,706 | 4/1987 | Messerschmidt et al. | 250/341 |

Primary Examiner—F. L. Evans
Attorney, Agent, or Firm—Calfee, Halter & Griswold

[57] ABSTRACT

A spectroscopy system separates the diffuse reflectance component of a reflectance spectrum from the specular reflectance component using a remote field stop filter. The surface of the sample is placed at a focal plane of an optical system. The optical system forms an image on the surface of the sample that includes an image of the remote field stop filter. The optical system images the surface of the sample onto either the same or another remote field stop. Energy reflected from the surface of the sample which is in focus at the remote field stop retains the image information about the image of the filter, whereas energy reflected from below the surface of the sample does not necessarily retain image information about the image of the filter. Since the energy from the surface of the sample is specularly reflected and the energy from below the surface is diffusely reflected, the specular component of the reflectance spectrum is spatially separate from some of the diffuse reflection component at the remote image stop and is filtered out. The now filtered reflection spectrum contains diffusely reflected energy, which is directed to the detector of a spectrometer.

15 Claims, 4 Drawing Sheets

Fig. 4

DIFFUSE REFLECTANCE SPECTROSCOPY SYSTEM AND METHOD

FIELD OF THE INVENTION

The present invention relates to the field of spectroscopy, and particularly to the field of diffuse reflectance infrared Fourier transform (DRIFT) spectroscopy.

DESCRIPTION OF RELATED ART

A reflectance spectrum of a powdered, granular material or a ground material in a matrix typically consists of two different spectroscopic components which correspond to energy that is specularly reflected from the surface of the sample and energy that is diffusely reflected from within the sample. Specularly reflected energy contains spectroscopic features that are derived from the surface of the sample, these features often change in response to any change at the surface. Often, specular reflectance spectra cannot be easily compared to a specular reflectance reference spectrum to identify a sample material.

In contrast, diffusely reflected energy enters the sample and/or sample matrix before reflecting. The spectroscopic features of a diffuse reflectance spectrum, like the features of a transmittance spectrum, are unique to a particular material. The reference spectrum of a material can be established for diffuse reflectance and compared against a known diffuse reflectance spectrum to identify the composition of the sample, including its components and the concentration percentages of those components. Sample identification and/or sample component concentrations therefore require obtaining the spectrum of diffusely reflected energy separate from the spectrum of specularly reflected energy.

Various spectroscopic systems have been devised to separate the diffuse component of a reflection spectrum from the specular component. Several of these spectroscopic systems work on the aperture exclusion principle first advanced by Fuller and Griffiths. The aperture exclusion principle assumes that the surface of the sample tends to behave like a mirror. A well defined beam of incident energy specularly reflects off the sample according to Snell's law and forms a somewhat well defined beam of specularly reflected energy. The specularly reflected energy is thus largely confined to a known area of the aperture of a collecting mirror. Energy in all other regions is presumed to have been diffusely reflected. The region of the aperture having the specularly reflected energy is obstructed so that some or all of the diffusely reflected energy is directed to the detector.

The aperture exclusion principle works only so long as the sample behaves like a mirror. Many materials, however, have a granular surface. The incident radiant energy specularly reflects from each grain according to its particular orientation and size relative to the wave length of the incident energy. The cumulative effect of specular reflection from all the grains in an illumination area is a phenomenon that is called specular scatter. Specular scatter can disperse specularly reflected energy over all angles of reflection. Some materials exhibit so much specular scatter that specularly reflected energy is distributed somewhat evenly over all angles of reflection and the specular component of the reflectance spectrum is thus inseparable from the diffuse component at the aperture of the collecting mirror.

An alternative to aperture exclusion involves placing a blocker device on or closely adjacent to the surface of the sample to block out specularly reflected energy, as is shown, for example, in U.S. Pat. No. 4,661,706 owned by the assignee of the present invention. A beam of incident energy is incident to the sample on one side of the blocker and diffusely reflected energy is collected from the other side of the blocker. The incident energy must penetrate into the sample to get under the blocker and reach the detector. Thus, the detector receives only diffusely reflected energy. Experiments have repeatedly shown that the blocker device removes essentially all specularly reflected energy from a reflectance spectrum.

The blocker device, however, has some limitations. The incident side of the blocker should diffusely reflect more energy since it has more total energy. The blocker thus prevents a majority of the diffusely reflected energy from reaching the detector. Moreover, a common reason for taking a reflectance spectrum, in preference to a conventional transmittance spectrum, is that the sample is opaque to the source energy. Thus, diffuse reflection usually only occurs from regions of the sample that are near the surface. The blocker device therefore has the unintended effect of limiting the sample area to a region that is adjacent to the blocker. The relatively low throughput efficiency and limited sample size obtained using the blocker device are undesirable attributes in some applications, such as quality control that involve sampling macroscopic samples without regard to microscopic inhomogeneities.

There exists a need for a diffuse reflectance optical system that has a high throughput efficiency as well as good exclusion of specularly reflected energy from samples that exhibit specular scatter.

SUMMARY OF THE INVENTION

The present invention contemplates a diffuse reflectance system that uses a new principle of focal plane differentiation to extract the diffuse reflectance component of a reflectance spectrum. Many samples that exhibit substantial amounts of specular scatter have a well defined surface with many small grains of specularly reflecting material. Thus, the present invention presumes that specular reflection and specular scatter occur at a well defined plane, such as the surface of a sample, and that diffuse reflection occurs from within the sample or sample/matrix combination. For sample surfaces having relatively small grains, the specular reflection and specular scatter components of the reflectance spectrum are filtered at a remote field stop plane that corresponds to a sample image plane. Diffuse energy in the sample reflection spectrum which appears to emanate from areas not excluded by the image of the filter is directed to a detector of a spectrometer, such as a conventional FT-IR spectrophotometer. The effectiveness of the image plane filter at eliminating specular scatter depends upon the extent to which specular scatter is confined to a well defined optical plane at the surface of the sample, the extent to which the energy penetrates the sample or sample matrix, the numerical aperture of the observing system, and the imaging quality of the observing system.

In the preferred embodiment of the present invention the sample is placed at a focal plane of an optical system. The optical system forms an image on the surface of the sample that includes optical information about a remote field stop filter or splitter. The optical system then images the surface of the sample onto the remote field stop. Specularly reflected energy from the surface of the sample is in focus and therefore retains the image information about the image of the filter. In contrast, energy that is diffusely reflected from within the sample is out of focus and spread across the field stop. Assuming that the energy from the surface of the sample is specularly reflected and the energy from within the sample is diffusely reflected, the specular component of the reflectance spectrum is spatially confined to certain select areas or bands where it is excluded, for example, by reflecting it back to the source. Part of the diffusely reflected energy not confined to those select areas is directed by the field stop filter to the detector.

The field stop filter may comprise a reflective area beam splitter having an array of reflective surfaces with reflective "islands", including, for example, a grid of reflective flat wires or reflective faces. The reflective surfaces that receive the incident energy from the source need have no particular symmetry relative to the optical axis of the optical system. The optical system images the incident reflective areas of the filter onto the sample and images energy reflected from the sample onto the filter. Radiant energy specularly reflected from the surface of the sample is in focus and reflects back onto the incident reflective areas of the filter to be discarded from the system. Some of the radiant energy diffusely reflected from within the sample is out of focus. Thus, part of this defocused, diffusely reflected energy fills areas between the incident reflective areas of the filter. The spatial separation of the components of the reflection spectrum at the field stop filter permits the defocused, diffusely reflected energy to be directed to a detector.

The optical system may also include a first field stop grid filter, a refractive beam splitter and a second grid filter. The first grid filter is the negative of the second field stop grid filter, meaning that energy going through the first filter and remaining in focus through the rest of the optical system will be blocked by the second filter. The optical system forms an image on the surface of the sample that includes optical information about the first grid filter. The optical system then images the surface of the sample onto the second grid filter. Specularly reflected energy from the sample is in focus and is thus blocked by the second filter while diffusely reflected energy from the sample passes though the second grid filter to a detector.

The incident reflective areas or incident grid transmissive areas are spaced close together to better define a flat sample image plane. To avoid significant diffraction effects, the spacing between incident reflective areas or grid areas, however, must be larger than X where $$X = LRS = \frac{0.61\lambda}{NA}.$$

In that equation, LRS is the least resolvable separation, $\lambda$ is the wavelength of the energy and NA is the numerical aperture of the optical system. The relative size and spacing of the reflective areas may increase with the granularity of the sample to partially compensate for the rougher surface of a granular sample by still being able to eliminate most specular scatter from the system by back reflection off the larger incident reflective areas.

By utilizing one or more remote field stop filters to separate the diffusely reflected energy from the specularly reflected energy in the reflectance spectrum, the present invention has eliminated the effect of the morphalogy or microscopic geography of the sample or sample matrix. The present invention does not require the sample to be heated, mixed, stirred or treated in any manner for the spectroscopic analysis to be made.

The present invention further contemplates large scale area sampling to reduce the effects of localized heterogeneity and to improve the signal to noise ratio of the resulting spectrum. The scaling is most simply accomplished by increasing the focus area on the surface of the sample. A focus area diameter of between 1 mm and 25 mm is thought to have particular utility for infrared measurement of substances in a quality control environment. However, the present invention is not limited to this focus area diameter and has been used in conjunction with an IR microscope accessory.

DETAILED DESCRIPTION OF THE PREFERRED EMBODIMENT

Figures 1A, 1B, 1C:
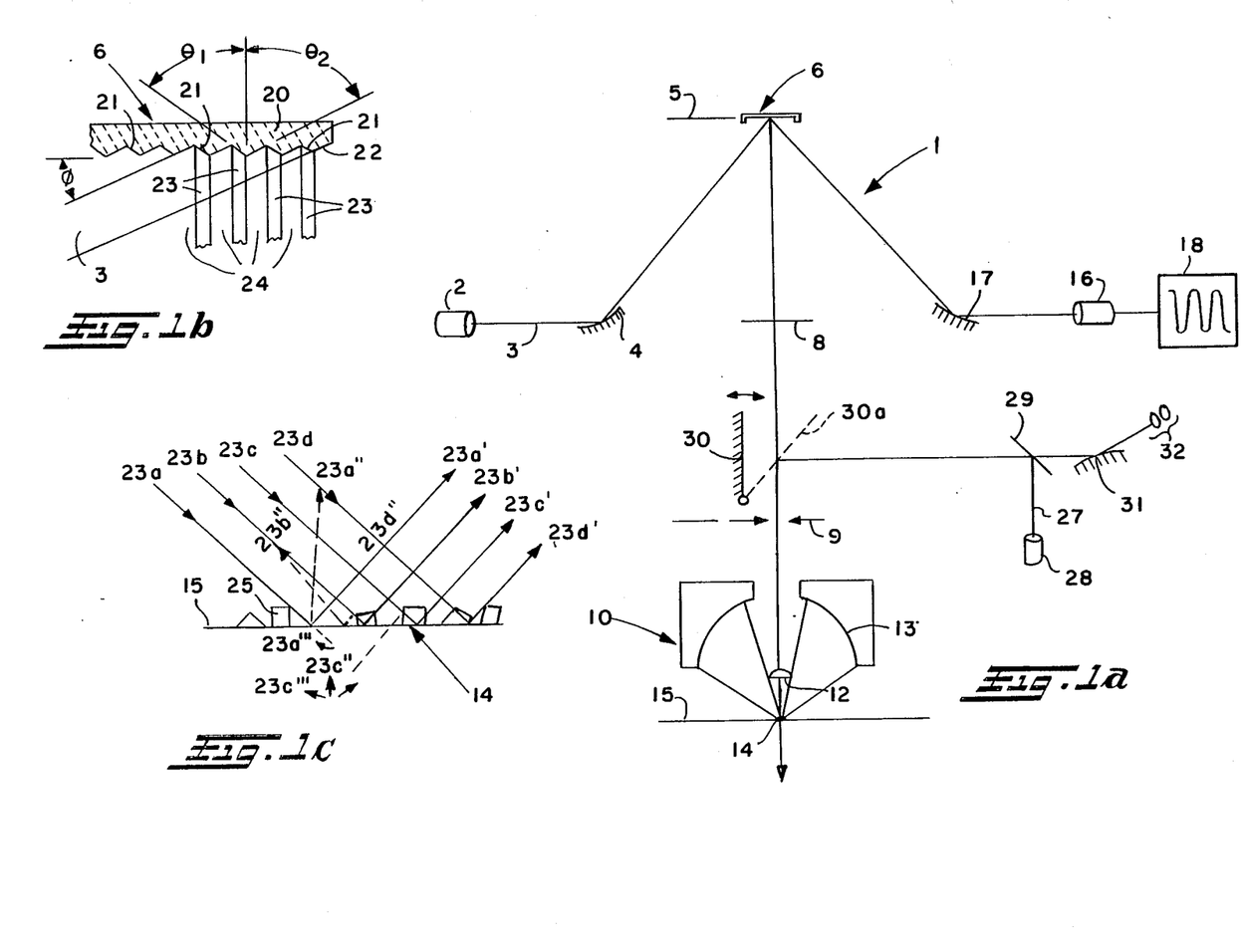
FIG. 1a schematically illustrates a diffuse reflectance optical system that uses a faceted splitter at a field stop to filter out the specular component of a diffuse reflectance spectrum.
FIG. 1b is an enlarged detail view of the faceted splitter of FIG. 1a illustrating the energy input to, energy output from and reflectance patterns of the saw tooth reflective surface of the faceted splitter.
FIG. 1c is a greatly magnified, detail elevation of a sample area having an irregular granular surface at the sample plane of the optical system, the elevation schematically illustrating some input energy that is specularly reflected, some input energy that is specularly scattered and some input energy that is diffusely reflected from the sample.

FIG. 1a shows an embodiment of a diffuse reflectance spectroscopy system, indicated generally at 1, that uses a filter or mask at a field stop. The system 1 includes an energy source 2 directing a beam of energy 3 through the system. The terms energy or energy beam as used herein encompass energies of different wavelengths from visible light through the radiant energy spectrum, with infrared energy being preferred.

Energy beam 3 is reflected from a concave transfer mirror 4 to a focus at a field stop plane 5. A filter, indicated generally at 6, is positioned at field stop plane 5. As discussed in more detail below, the filter 6 is preferably a faceted beam splitter having input faces reflecting the incident energy in spaced bands in a normal direction from the field stop plane. A condensing lens mirror system 8 focuses the spatially banded energy at a remote image plane mask 9. The energy emanating from the remote image plane mask 9 enters a Cassegranian lens, indicated generally at 10. The Cassegranian lens 10 includes a secondary mirror 12 and a primary mirror 13 operative to focus the incident energy onto a sample area 14 on sample plane 15.

The sample 14 comprises a granulated powder material or a ground material in a matrix. The sample may be a single material or may be comprised of a number of constituent or component materials. The sample does not have to be specially treated or mixed, but instead can be placed on the sample plane in its untreated state for analysis.

Energy specularly reflected from the sample area is returned to and imaged at remote image plane mask 9 and filter 6. As explained below, the filter 6 reflects focused, specularly reflected energy back to mirror 4, while directing defocused, primarily diffusely reflected energy to detector 16 by way of concave transfer mirror 17. The detector 16 receives the diffusely reflected energy and converts the same into spectroscopic data about the sample area, the data being available to the researcher for analysis at the data terminal 18. From this diffuse reflectance data, the researcher can identify the composition of the sample and its constituents, including the concentration percentages of those constituents.

In use, the image of the incident reflective face of faceted splitter or filter 6 at field stop plane 5 is spatially defined or imaged at remote image plane mask 9 before being imaged onto sample 14 at sample plane 15. The energy forms an odd number of image planes so that energy that is specularly reflected from sample 14 returns to the incident face of the faceted splitter from which it was originally reflected. The focused energy returned from the sample area is thus reflected by the faceted splitter 6 back to source 2. Some defocused energy returned from sample 14 is contained in bands between the incident or input faces of the faceted beam splitter and thus strikes other output faces of the faceted splitter 6 for reflection of this defocused energy to output detector 16.

FIG. 1b aids in understanding the structure and operation of faceted splitter 6. The faceted splitter 6 includes a body 20 having a saw tooth edge or cross section forming a plurality of parallel input faces 21 and a plurality of parallel output faces 22. The input faces 21 are inclined at an angle $\theta_1$ relative to a normal to the field stop plane output faces 22 are oppositely inclined at an angle $\theta_2$ relative to the normal.

The incoming incident energy forms an angle $\phi$ with respect to the field stop plane 5. The incident energy beam from source 2 impinges upon the reflective surfaces on each individual input face 21 in the beam's path. The angle of the incident energy $\phi$ and input face angle $\theta_1$ are chosen such that the radiant energy reflects from the input faces 21 in a direction along the optical path of the system. Since the incident energy is striking a plurality of spaced parallel input faces 21, the normally reflected energy leaves the faceted splitter in a pattern of generally parallel energy bands, schematically illustrated in shaded band areas 23. The bands of energy 23 are separated by bands 24 without energy from the source, the bands 24 being aligned with output faces 22 which do not reflect energy from the source because of their orientation.

The image of faceted splitter 6 is projected by the banded incident energy 23 onto sample 14 of sample plane 15. The splitter image comprises a series of energy bands corresponding to the incident reflective surfaces of each incident input face 21 of the faceted splitter.

FIG. 1c aids in understanding the interaction of the radiant energy with the sample surface area of a diffusely reflecting sample which exhibits specular scatter. A granular sample surface having an irregular surface contour 25 is shown of the type typically encountered with diffusely reflecting material.

Incident energy bands 23a–d would be specularly reflected, as though from a mirror, at the sample focal plane to form beams 23a'–d' but for the presence of surface discontinuities or irregularities introduced by the granular nature of the sample. The incident energy beams partially scatter by reason of being irregularly reflected off the contoured surface of each grain near the focal plane as emplified by beams 23a''–d''. However, since the granules are normally relatively small, the specularly scattered reflections 23a''–d'' off the granules normally occur fairly close to the sample focal plane. As such and because of the relative size and spacing of input faces 21, the specularly reflected energy 23a''–d'' is still mainly in focus with the optic system. The specular reflective energy 23a'–d' and specular scattered energy 23''–d'' by being in focus retain the information about the image of the splitter at the sample and thus return to the splitter in bands 23a–d to strike the same input faces 21 of the splitter. The specular reflections returning from the surface of sample 14 are reflected by input faces 21 back toward the source 2 to effectively be discarded or filtered from the system.

Some of the incident energy 23a–d may penetrate the surface of sample 14 and invade that sample before being diffusely reflected back out of the sample as schematically illustrated at 23a'''–d'''. The diffuse reflectance energy 23a'''–d''' is spread across the entire optical path as it returns through the optical system to the faceted beam splitter for filtering. Thus, some of the diffusely reflected energy from the sample area will return to faceted splitter 6 in the bands 24 between the focused energy bands 23. This defocused diffusely reflected energy in bands 24 appears to emanate from surface areas not excluded by the image of the filter at the sample. This defocused or filtered energy will strike output faces 22 on the faceted splitter and be directed to the detector 16. Thus, faceted splitter 6 separates or filters the energy by where the energy emanates from relative to the focused image of the faceted splitter at sample plane 15, so that only the defocused, presumably diffusely reflected radiant energy is reflected to detector 16.

The relative efficiency of the present invention in separating the specular and diffuse components of the reflective spectrum from the sample depends on the spacing of the faces 21 and 22 on faceted splitter 6 relative to the depth of penetration of the energy at the sample area compared to the focused image of the splitter at sample plane 15. A sample area having shallow depth of energy penetration requires that the faces 21 and 22 on faceted splitter 6 be placed closely together so that the surface of the sample area is almost uniformly energized. Conversely, a sample area, which has a large depth of energy penetration, should have larger faces 21 and 22 separated by larger distances.

The upper limit of the spacing of the faces of the faceted splitter 6 is determined by design and sampling considerations. For example, the size and separation of the faces 21 and 22 of splitter 6 should be correlated to the wave length of the incident energy. In addition, the faces 21 and 22 should be separated by a sufficient distance that the faceted splitter 6 does not produce significant diffraction effects.

The location of the sample is particularly critical in that the sample surface must be located at a good quality optical focus. One method of positioning the sample at a good focus is to direct visible light along part of the same optical path as the sampling energy and to use the visual observation system shown in FIG. 1a to focus that visible light at the sample plane 15.

In this regard, a portion of a beam of visible light 27 from lamp 28 reflects off refractive beam splitter 29 to a pivotable mirror 30. If pivotal mirror 30 is arcuately moved into the optical path of the energy as illustrated by the dotted line 30a, the energy from source 1 is blocked and visible light from lamp 28 is reflected off mirror 29. This reflected visible light is focused at remote image plane mask 9 so that secondary mirror 12 and primary mirror 13 focus the visible light onto the same sample plane that the radiant energy is focused upon in the sampling mode. Part of the reflected light passes through refractive beam splitter 29 to mirror 31 where it may be observed with eyepiece 32. In the visible light viewing mode, the user can adjust the mask 9 to vary the size of the opening at the remote image plane to control the size of the surface area being sampled and can vertically adjust the sample plane to bring the optical system into proper focus for subsequent radiant energy sample testing.

It is to be appreciated that the optical system shown in FIG. 1a may comprise either a low magnification sampling system or a high magnification microscope.

Figure 2:
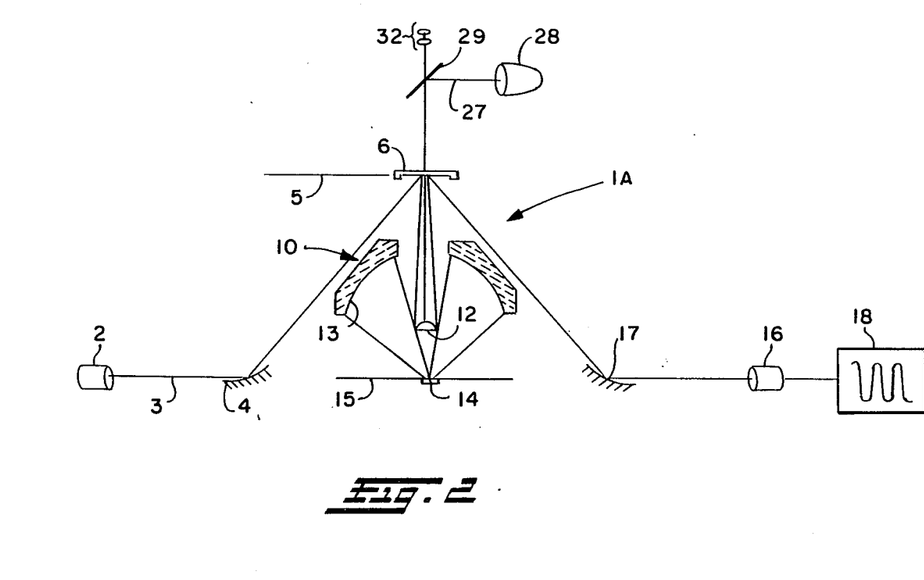
FIG. 2 is an alternate embodiment of the system shown in FIG. 1 that includes a simplified optics system for macrosampling purposes.

FIG. 2 illustrates a simplified version of the system shown in FIG. 1 that is particularly well adapted to macrosampling of sample surface areas for quality control purposes. The structural elements in the FIG. 2 embodiment that are common with the structural elements of the FIG. 1 embodiment are identified by the same reference numerals. As is apparent from comparing the common reference numerals and as described in more detail below, the diffuse reflectance spectroscopy system 1A of FIG. 2 is very similar to the FIG. 1 embodiment except that the remote image plane mask and associated lenses are eliminated and the visible viewing system simplified.

In FIG. 2, concave transfer mirror 4 focuses energy from source 1 onto input faces of faceted splitter 6. Secondary mirror 12 directs the energy reflected from faceted splitter 6 to primary mirror 13. Mirror 13 forms an image of faceted splitter 6 on sample 14 at sample plane 15.

Primary mirror 13 collects the energy reflected from sample 14 so that it is returned to faceted splitter 6 by secondary mirror 12. The faceted splitter 6 separates specularly reflected energy from sample 14 from energy that is diffusely reflected from within the sample area surface as explained above. The input faces 21 of the faceted splitter return focused energy specularly reflected from the sample to the source while the output faces 22 of the faceted splitter direct unfocused energy diffusely reflected from the sample to the detector 16 by way of concave transfer mirror 17.

The macrosampling system shown in FIG. 2 can also comprise means for automatically positioning a plurality of samples 14 at the focus of primary mirror 13. For example, samples 14 may be sequentially moved into position on an endless track or conveyor including a plurality of sample holders.

The optical system of the macrosampling apparatus shown in FIG. 2 may be focused in a visible light viewing mode. The visible light viewing system includes a lamp 28 producing a visible light beam 27, which is reflected along the optical path of the radiant energy by refractive beam splitter 29. The eyepiece 32 is positioned in axial alignment with that optical path. Sample plane 15 may be visually observed by pivoting or sliding faceted splitter 6 out of the optical path of eyepiece 32. Visible light beam 27 reflects off refractive beam splitter 29 to sample plane 15 and returns through refractive beam splitter 29 to eyepiece 32. Alternately, the source of visible light may be placed between the primary mirror and the sample so that eyepiece 32 receives a "dark field" view of sample image plane 15. Aligned eyepiece 32 permits aligning and focusing sample plane 15 and the sample 14 thereon at the focus of primary mirror 13.

Figures 3, 3A:
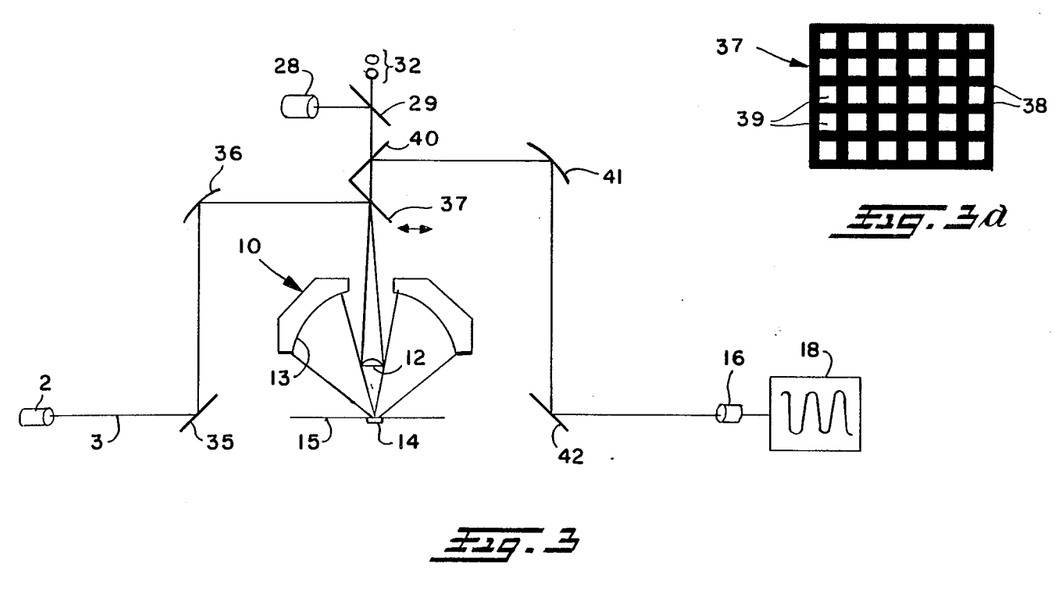
FIG. 3 is an alternate embodiment of the diffuse reflectance optical system shown in FIG. 2 wherein the faceted splitter is replaced with a reflective area beam splitter.
FIG. 3a is an elevation of a wire grid used as the filter at the field stop plane in the FIG. 3 embodiment.

FIG. 3 shows an alternate embodiment of the diffuse reflectance spectrometer apparatus shown in FIG. 2 utilizing a different type of filter or mask at the field stop plane. Transfer mirrors 35 and 36 direct radiant energy 3 from source 2 to a focus at a filter 37, such as an "island" splitter or wire grid. The filter 37 may take numerous forms having different patterns of reflective surfaces or different patterns of reflective surface areas coupled with transmissive surface areas or open areas. As shown for example in FIG. 3a, the filter 37 may have a crossing grid of reflective wires 38 defining a pattern of open transmissive areas 39. The reflective wires 38 are analogous to input faces 21 on splitter 6 while open transmissive areas 39 are analogous to output faces 22.

The incident energy reflected in patterned bands from filter 37 enter secondary mirror 12 and primary mirror 13 of Cassegranian lens 10 to focus the diverging beam of banded radiant energy at sample plane 15. A focused image of the filter 37 is formed at the sample plane 15 by the energy striking the sample 14.

Incident radiant energy that is specularly reflected from the sample 14 at sample plane 15 is imaged onto the reflective regions of filter 37 so as to be lost from the system by being reflected back toward source 2. As described above, some of the incident radiant energy that is diffusely reflected from the sample is out of focus and passes between the reflective regions of filter 37 to mirror 40. Transfer mirrors 41 and 42 direct the diffusely reflected radiant energy from mirror 40 to detector 16. Reflective area splitter or filter 37 thus functions in much the same manner as the reflective faceted splitter 6 of FIG. 1a except that the diffusely reflected radiant energy passes between the reflective areas rather than reflecting off output faces having reflective surfaces.

The embodiment of FIG. 3 also has a visible light viewing and focusing system as described in conjunction with FIG. 2 including lamp 28, refractive beam splitter 29 and eyepiece 32 axially aligned with the optical path. When mirror 40 and splitter 37 are slid or pivoted out of the way, visible light is focused on the sample 14 by Cassegranian lens 10, with the sample image being viewed in eyepiece 32 to allow adjustment of sample plane 15 to bring the optical system into focus.

Figure 4:
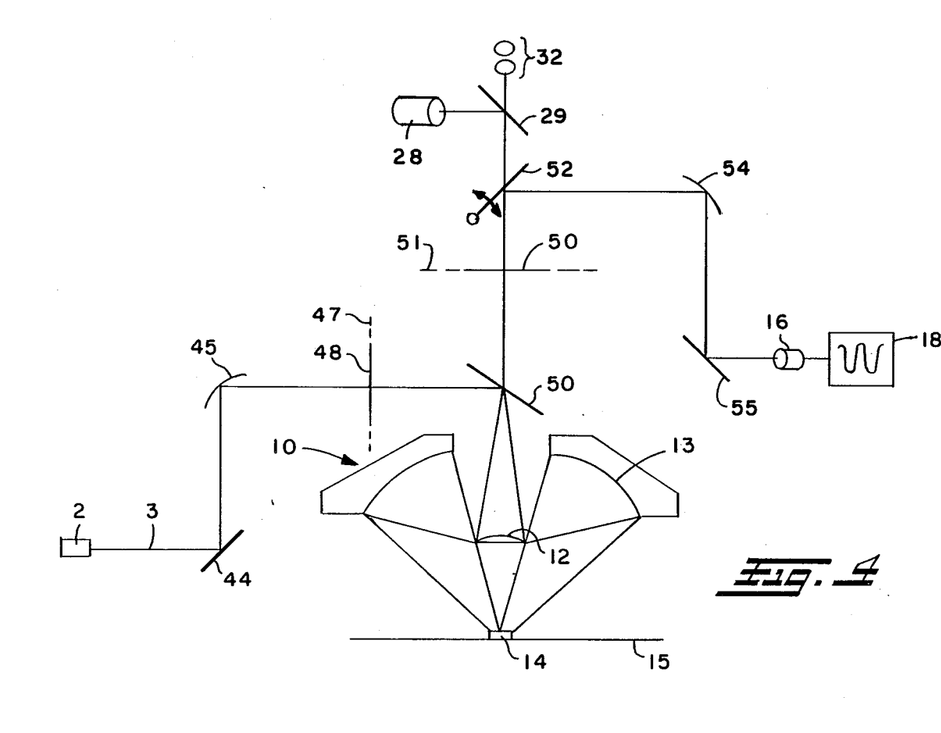
FIG. 4 is an alternate embodiment of the system shown in FIG. 1 including first and second remote field stop filters and a refractive beam splitter.

FIG. 4 shows alternate embodiment of the diffuse reflectance spectrometer apparatus shown in FIGS. 1 through 3 utilizing two filters at two discrete field stop planes and a refractive beam splitter. Transfer mirrors 44 and 45 direct radiant energy 3 from source 2 to a focus at a first remote field stop plane 47. A first filter 48 is positioned in the field stop plane in the optical path of the system. First filter 48 comprises a grid having crossed reflective wires 38 defining open transmissive areas 39 therebetween as illustrated in FIG. 3A.

The radiant energy striking the reflective wire grids is discarded from the system. The energy passing through the open or transmissive areas 39 in first grid filter 48 is directed in discrete energy bands toward refractive beam splitter 50. The incident energy bands reflected from refractive beam splitter 50 enter secondary mirror 12 and primary mirror 13 of Cassegranian lens 10 to focus the banded radiant energy at the sample 14 on sample plane 15. A focused image of the first grid filter 48 is formed at the sample plane 15 by the energy striking the sample 14.

Primary mirror 13 collects the energy reflected from sample 14 so that it is returned to refractive beam splitter 50 by secondary mirror 12. Some of the energy reflected from sample 14 passes through the refractive beam splitter 50 to a second wire grid filter 50 positioned at a second remote field stop plane 51. The second wire grid filter 50 is positioned the same distance from refractive beam splitter 50 as is the first grid filter 48. The second grid filter 50 is a negative to or a complement of the first grid filter 48 meaning that energy going through the first filter and remaining in focus through the rest of the optical system will be blocked by the reflective wires of the second grid filter 50.

As discussed above, the specularly scattered and specularly reflected energy from sample 14 will remain in focus and will be discarded from the system by being reflected from the wire grids 38 of second filter 50. The diffusely reflected energy from sample 14 will be spread across the entire reflectance spectrum, with that diffusely reflected energy positioned between the bands of focused energy passing through the open or transmissive areas 39 of second filter 50 to pivotal mirror 52. Transfer mirrors 54 and 55 direct the diffusely reflected radiant energy from pivotal mirror 52 to detector 16.

The embodiment of FIG. 4 also has a visible light viewing and focusing system as described in conjunction with FIGS. 2 and 3. This visible light system includes lamp 28, refractive beam splitter 29 and eyepiece 32 axially aligned with the optical path. When mirror 52 is pivoted out of the optical path, visible light is focused on sample 14 by Cassegranian lens 10, with the sample image being viewed in eyepiece 32 to allow vertical adjustment of sample plane 15 to bring the optical system into focus.

The principles, preferred embodiments and modes of operation of the present invention have been described in the foregoing specification. The invention which is intended to be protected herein should not, however, be construed as limited to the particular forms described as these are to be regarded as illustrative rather than restrictive. Variations and changes may be made by those skilled in the art without departing from the spirit of the invention. For example, the optical systems could all be inverted with the incident energy striking the sample from below rather than from above. In such case, the sample would be supported from below by an energy transmitting window. This orientation may provide some advantages, such as being able to utilize a smaller quantity of sample to perform the analysis. Accordingly, the foregoing detailed description is considered exemplary in nature and not as limiting to the scope and spirit of the invention set forth in the appended claims.

We claim:

1. A diffuse reflectance spectroscopy system comprising:
   a source of energy;
   a sample at a sample plane;
   means to direct the energy from the source of energy to a focus at a field stop plane;
   a filter at the field stop plane operative to reflect the energy from the source of energy toward the sample in spatially separated energy bands; and
   means to direct the energy bands onto the sample at the sample plane in focus to form an image of the filter at the sample plane and to return energy reflected from the sample to the filter;
   the filter being operative to direct specularly reflected focused energy from the sample out of the system and to direct diffusely reflected unfocused energy from the sample to a detector.

2. The diffuse reflectance spectroscopy system of claim 1 wherein the filter is a beam splitter having a saw tooth cross section forming a plurality of parallel reflective input faces inclined in one direction and a plurality of parallel, reflective output faces inclined in another direction, the input faces reflecting the energy from the source to form the energy bands and reflecting the focused energy specularly reflected from the sample out of the system and the output faces reflecting the unfocused energy diffusely reflected from the sample to the detector.

3. The diffuse reflectance spectroscopy system of claim 1 wherein the filter has a pattern of reflective and non-reflective areas, the reflective areas of the beam splitter reflecting the energy from the source to form the energy bands and reflecting the focused energy specularly reflected from the sample out of the system and the non-reflective areas passing the unfocused energy diffusely reflected from the sample to the detector.

4. The diffuse reflectance spectroscopy system of claim 1 wherein the energy source supplies radiant energy and the means to direct and to return includes a Cassegranian lens positioned adjacent the sample plane.

5. The diffuse reflectance spectroscopy system of claim 4 further comprising a condensing lens operative to focus the bands of radiant energy at a remote image plane between the filter and the Cassegranian lens.

6. The diffuse reflectance spectroscopy system of claim 4 further comprising a visible light viewing system including a source of visible light, means to direct the visible light along an optical path to the sample corresponding to that of the radiant energy and viewing means to view an image of the sample in visible light along the optical path for focusing or positioning purposes.

7. The diffuse reflectance spectroscopy system of claim 5 further comprising a visible light viewing system including a source of visible light, means to direct the visible light along an optical path to the sample corresponding to that of the radiant energy and viewing means to view an image of the sample in visible light along the optical path for focusing or positioning purposes.

8. The diffuse reflectance spectroscopy system of claim 7 further comprising a mask at the remote image plane, the mask being adjusted in the visible light viewing mode to target a surface area of the sample for radiant energy sampling.

9. A diffuse reflectance spectroscopy system comprising:

a source of energy;

a sample at a sample plane;

means to direct the energy from the source of energy to a focus at a first field stop plane;

a first filter at the first field stop plane operative to direct energy from the source of energy toward the sample in spatially separated bands;

means to direct the energy bands onto the sample plane in focus to form an image of the first filter at the sample plane and to return energy reflected from the sample to a second filter at a second field stop plane;

the second filter being operative to direct specularly reflected focused energy from the sample out of the system and to direct diffusely reflected unfocused energy from the sample to a detector.

10. The diffuse reflectance spectroscopy system of claim 9 wherein the first and second filters are wire grids having opposite reflective and transmissive patterns so that the second filter is a complement to the first filter.

11. The diffuse reflectance spectroscopy system of claim 10 wherein the means to direct and return includes a refractive beam splitter and a Cassegranian lens.

12. A method of obtaining a diffuse reflectance spectrum in an optical system comprising the steps of:
introducing radiant energy into the system;
focusing the radiant energy at a field stop;
positioning a filter at this field stop;
reflecting incident radiant energy from the source off of the filter to form discrete radiant energy bands;
directing the radiant energy bands to a focus at a sample plane containing a sample, an image of the filter being formed at the sample plane;
collecting the specularly and diffusely reflected radiant energy from the sample and returning the same to the filter;
dividing specularly reflected sample energy from diffusely reflected sample energy at the filter; and
directing only the diffusely reflected energy from the filter to a detector.

13. The method of claim 12 further comprising the steps of
focusing the energy bands at a remote image plane and
masking the remote image plane to define the surface area of the sample being contacted by radiant energy.

14. The method of claim 13 further comprising the steps of
directing visible light along an optical path corresponding to that of the radiant energy and
viewing an image of the sample in visible light to focus the optics or position the sample.

15. A method of obtaining a diffuse reflectance spectrum in an optical system comprising the steps of:
introducing radiant energy into the system;
focusing the radiant energy at a first field stop;
positioning a first filter at the first field stop to form discrete energy bands;
directing the discrete radiant energy bands to a focus at a sample plane containing a sample,
forming an image of the first filter at the sample plane;
collecting diffusely and specularly reflected radiant energy from the sample and returning the same to a second filter at a second field stop plane;
dividing specularly reflected sample energy from the diffusely reflected sample energy at the second filter;
and directing only the diffusely reflected energy from the second filter to a detector.

* * * * *

Disclaimer and Dedication 4,859,064—Robert G. Messerschmidt, Westport; Donald W. Sting, New Cannan, both of Conn. DIFFUSE REFLECTANCE SPECTROSCOPY SYSTEM AND METHOD. Patent dated August 22, 1989. Disclaimer and Dedication filed June 15, 2001, by the assignee, Spectra-Tech, Inc.

Hereby disclaims and dedicates to the Public all claims and entire term of said patent.
*(Official Gazette, August 14, 2001)*